(12) United States Patent
Wagner et al.

(10) Patent No.: US 6,454,769 B2
(45) Date of Patent: Sep. 24, 2002

(54) SYSTEM AND METHOD FOR STABILIZING THE HUMAN SPINE WITH A BONE PLATE

(75) Inventors: Erik J. Wagner; Robert Jones, both of Austin, TX (US)

(73) Assignee: Spinal Concepts, Inc., Austin, TX (US)

( * ) Notice: Subject to any disclaimer, the term of this patent is extended or adjusted under 35 U.S.C. 154(b) by 0 days.

(21) Appl. No.: 09/089,027

(22) Filed: Jun. 2, 1998

Related U.S. Application Data

(63) Continuation-in-part of application No. 08/905,823, filed on Aug. 4, 1997, now abandoned.

(51) Int. Cl.[7] ............................................... A61B 17/70
(52) U.S. Cl. ............................. 606/69; 606/61; 606/73
(58) Field of Search .............................. 606/61, 72, 73, 606/69, 70, 71

(56) References Cited

U.S. PATENT DOCUMENTS

| | | | |
|---|---|---|---|
| 4,388,921 A | * 6/1983 | Sutter et al. | ................... 606/71 |
| 4,401,112 A | 8/1983 | Rezaian | |
| 4,433,677 A | 2/1984 | Ulrich et al. | |
| 4,492,226 A | 1/1985 | Belykh et al. | |
| 4,501,269 A | 2/1985 | Bagby | |
| 4,503,848 A | 3/1985 | Caspar et al. | |
| 4,570,618 A | 2/1986 | Wu | |
| 4,604,995 A | 8/1986 | Stephens et al. | |
| 4,641,636 A | 2/1987 | Cotrel | |
| 4,643,178 A | 2/1987 | Nastari et al. | |
| 4,743,256 A | 5/1988 | Brantigan | |
| 4,763,644 A | 8/1988 | Webb | |
| 4,805,602 A | 2/1989 | Puno et al. | |
| 4,834,757 A | 5/1989 | Brantigan | |
| 4,863,476 A | 9/1989 | Shepperd | ..................... 623/17 |
| 4,878,915 A | 11/1989 | Brantigan | |
| 4,887,596 A | 12/1989 | Sherman | |
| 4,946,458 A | 8/1990 | Herma et al. | |

(List continued on next page.)

FOREIGN PATENT DOCUMENTS

| | | |
|---|---|---|
| DE | 43 23 956 C1 | 10/1994 |
| EP | 0 260044 A1 | 3/1988 |
| EP | 0578320 A1 | 1/1994 |
| FR | 2 717 068 | 9/1995 |
| FR | 2732887 A1 | 10/1996 |
| FR | 2736535 A1 | 1/1997 |
| SU | 1424826 A | 9/1988 |
| WO | 97/00054 | 1/1997 |
| WO | 97/06753 | 2/1997 |

OTHER PUBLICATIONS

Danek Group, Inc. Medical Division Publication entitled, "TSRH Spinal System—Unmatched versatility," 1992, pp. 1–4.

Danek Surgical Technique Manual entitled, "TSRH Spinal Implant System," Date Unknown, pp. 1–16.

Danek Surgical Technique Manual entitled, "TSRH Crosslink," Date Unknown, pp. 1–8.

(List continued on next page.)

Primary Examiner—David O. Reip
(74) Attorney, Agent, or Firm—Eric B. Meyertons; Conley, Rose & Tayon, P.C

(57) ABSTRACT

A spinal plate system and method for fixation of the human spine is provided. In an embodiment, the system includes a bone plate, a bone screw and a ring. The bone screw preferably connects the bone plate to a bone, and the ring preferably fixes the bone screw into a borehole of the bone plate such that the bone screw extends from the bone plate at a selected angle. The ring is preferably capable of swiveling within the borehole to allow the bone screw to be angulated at a plurality of angles oblique to the plate. The bone screw may have a head having a tapered, threaded surface for engaging the ring. The ring preferably has threading on its inner surface for mating with the threading on the head. The inner surface of the ring may be tapered. Movement of the head through the ring preferably expands the ring against the bone plate to fix the bone screw at a selected angle relative to the bone plate.

98 Claims, 6 Drawing Sheets

U.S. PATENT DOCUMENTS

| | | | |
|---|---|---|---|
| 4,950,269 A | 8/1990 | Gaines, Jr. | |
| 4,961,740 A | 10/1990 | Ray et al. | |
| 4,966,600 A | 10/1990 | Songer et al. | |
| 4,987,892 A | 1/1991 | Krag et al. | |
| 5,005,562 A | 4/1991 | Cotrel | |
| 5,026,373 A | 6/1991 | Ray et al. | |
| 5,047,029 A | 9/1991 | Aebi et al. | |
| 5,053,036 A | * 10/1991 | Perren et al. | 606/69 |
| 5,055,104 A | 10/1991 | Ray | |
| 5,074,864 A | 12/1991 | Cozad et al. | |
| 5,102,412 A | 4/1992 | Rogozinski | |
| 5,108,399 A | 4/1992 | Eitenmuller et al. | |
| 5,108,446 A | 4/1992 | Wagner et al. | |
| 5,116,340 A | 5/1992 | Songer et al. | |
| 5,123,926 A | 6/1992 | Pisharodi | |
| 5,127,912 A | 7/1992 | Ray et al. | |
| 5,129,388 A | 7/1992 | Vignaud et al. | |
| 5,129,904 A | 7/1992 | Illi | |
| 5,147,359 A | 9/1992 | Cozad et al. | |
| 5,154,718 A | 10/1992 | Cozad et al. | |
| 5,171,278 A | 12/1992 | Pisharodi | |
| 5,176,678 A | 1/1993 | Tsou | |
| 5,176,680 A | 1/1993 | Vignaud et al. | |
| 5,181,917 A | 1/1993 | Rogozinski | |
| 5,192,321 A | 3/1993 | Strokon | |
| 5,192,327 A | 3/1993 | Brantigan et al. | |
| 5,201,734 A | 4/1993 | Cozad et al. | |
| 5,242,445 A | 9/1993 | Ashman | |
| 5,242,448 A | 9/1993 | Pettine et al. | |
| 5,246,442 A | 9/1993 | Ashman et al. | |
| 5,261,909 A | 11/1993 | Sutterlin et al. | |
| 5,263,953 A | 11/1993 | Bagby | |
| 5,281,222 A | 1/1994 | Allard et al. | |
| 5,282,801 A | 2/1994 | Sherman | |
| 5,290,312 A | 3/1994 | Kojimoto et al. | |
| 5,290,494 A | 3/1994 | Coombes et al. | |
| 5,303,718 A | 4/1994 | Krajicek | |
| 5,304,179 A | 4/1994 | Wagner | |
| 5,306,307 A | 4/1994 | Senter et al. | |
| 5,306,309 A | 4/1994 | Wagner et al. | |
| 5,312,405 A | 5/1994 | Korotko et al. | |
| 5,312,410 A | 5/1994 | Miller et al. | |
| 5,318,566 A | 6/1994 | Miller | |
| 5,336,223 A | 8/1994 | Rogers | |
| 5,336,240 A | 8/1994 | Metzler et al. | |
| 5,344,422 A | 9/1994 | Frigg | |
| 5,348,026 A | 9/1994 | Davidson | |
| 5,357,983 A | 10/1994 | Mathews | |
| 5,360,429 A | 11/1994 | Jeanson et al. | |
| 5,360,431 A | 11/1994 | Puno et al. | |
| 5,361,766 A | 11/1994 | Nichols et al. | |
| 5,364,399 A | 11/1994 | Lowery et al. | |
| 5,370,697 A | 12/1994 | Baumgartner | 623/17 |
| 5,380,325 A | 1/1995 | Lahille et al. | |
| 5,390,683 A | 2/1995 | Pisharodi | |
| 5,395,374 A | 3/1995 | Miller et al. | |
| 5,397,364 A | 3/1995 | Kozak et al. | |
| 5,403,315 A | 4/1995 | Ashman | |
| 5,405,391 A | 4/1995 | Hednerson et al. | |
| 5,415,658 A | 5/1995 | Kilpela et al. | |
| 5,417,690 A | 5/1995 | Sennett et al. | |
| 5,423,820 A | 6/1995 | Miller et al. | |
| 5,423,825 A | 6/1995 | Levine | |
| 5,425,772 A | 6/1995 | Brantigan | |
| 5,466,237 A | 11/1995 | Byrd, III et al. | |
| 5,474,555 A | 12/1995 | Puno et al. | |
| 5,480,437 A | 1/1996 | Draenert | |
| 5,484,437 A | 1/1996 | Michelson | |
| 5,489,307 A | 2/1996 | Kuslich et al. | |
| 5,489,308 A | 2/1996 | Kuslich et al. | |
| 5,496,318 A | 3/1996 | Howland et al. | |
| 5,505,732 A | 4/1996 | Michelson | |
| 5,507,746 A | 4/1996 | Lin | |
| 5,514,180 A | 5/1996 | Heggeness et al. | |
| 5,520,690 A | 5/1996 | Errico et al. | |
| 5,522,899 A | 6/1996 | Michelson | |
| 5,527,341 A | 6/1996 | Gogolewski et al. | |
| 5,531,746 A | 7/1996 | Errico et al. | |
| 5,531,751 A | 7/1996 | Schultheiss et al. | |
| 5,536,270 A | 7/1996 | Songer et al. | |
| 5,536,271 A | 7/1996 | Daly et al. | |
| 5,545,165 A | 8/1996 | Biedermann et al. | |
| 5,549,608 A | 8/1996 | Errico et al. | |
| 5,549,612 A | 8/1996 | Yapp et al. | |
| 5,554,157 A | 9/1996 | Errico et al. | |
| 5,563,124 A | 10/1996 | Damien et al. | |
| 5,569,248 A | 10/1996 | Mathews | |
| 5,569,253 A | 10/1996 | Farris et al. | |
| 5,571,192 A | 11/1996 | Schönhöffer | |
| 5,575,792 A | 11/1996 | Errico et al. | |
| 5,578,033 A | 11/1996 | Errico et al. | |
| 5,578,034 A | 11/1996 | Estes | |
| 5,584,834 A | 12/1996 | Errico et al. | |
| 5,586,984 A | 12/1996 | Errico et al. | |
| 5,593,409 A | 1/1997 | Michelson | |
| 5,601,553 A | 2/1997 | Trebing et al. | |
| 5,601,556 A | 2/1997 | Pisharodi | |
| 5,603,713 A | 2/1997 | Aust et al. | |
| 5,607,424 A | 3/1997 | Tropiano | |
| 5,607,425 A | 3/1997 | Rogozinski | |
| 5,607,426 A | 3/1997 | Ralph et al. | |
| 5,607,428 A | * 3/1997 | Lin | 606/69 |
| 5,607,430 A | 3/1997 | Bailey | |
| 5,609,592 A | 3/1997 | Brumfield et al. | |
| 5,609,593 A | 3/1997 | Errico et al. | |
| 5,609,594 A | 3/1997 | Errico et al. | |
| 5,609,596 A | 3/1997 | Pepper | |
| 5,609,635 A | 3/1997 | Michelson | |
| 5,609,636 A | 3/1997 | Kohrs et al. | |
| 5,611,800 A | 3/1997 | Davis et al. | |
| 5,611,801 A | 3/1997 | Songer | |
| 5,613,967 A | 3/1997 | Engelhardt et al. | |
| 5,616,144 A | 4/1997 | Yapp et al. | |
| 5,620,443 A | 4/1997 | Gertzbein et al. | |
| 5,624,441 A | 4/1997 | Sherman et al. | |
| 5,626,579 A | 5/1997 | Muschler et al. | |
| 5,628,740 A | 5/1997 | Mullane | |
| 5,628,756 A | 5/1997 | Barker, Jr. et al. | |
| 5,630,816 A | 5/1997 | Kambin | |
| 5,632,747 A | 5/1997 | Scarborough et al. | |
| 5,634,925 A | 6/1997 | Urbanski | |
| 5,643,260 A | 7/1997 | Doherty | |
| 5,643,264 A | 7/1997 | Sherman et al. | |
| 5,643,265 A | 7/1997 | Errico et al. | |
| 5,645,084 A | 7/1997 | McKay | |
| 5,645,544 A | 7/1997 | Tai et al. | |
| 5,645,549 A | 7/1997 | Bpyd et al. | |
| 5,645,598 A | 7/1997 | Brosnahan, III | |
| 5,647,873 A | 7/1997 | Errico et al. | |
| 5,649,927 A | 7/1997 | Kilpela et al. | |
| 5,651,283 A | 7/1997 | Runciman et al. | |
| 5,651,789 A | 7/1997 | Cotrel | |
| 5,653,708 A | 8/1997 | Howland | |
| 5,653,709 A | 8/1997 | Frigg | |
| 5,653,763 A | 8/1997 | Errico et al. | |
| 5,658,289 A | 8/1997 | Boucher et al. | |
| 5,658,337 A | 8/1997 | Kohrs et al. | |
| 5,658,516 A | 8/1997 | Eppley et al. | |
| 5,662,653 A | 9/1997 | Songer et al. | |
| 5,665,088 A | 9/1997 | Gil et al. | |
| 5,665,112 A | 9/1997 | Thal | |

| | | |
|---|---|---|
| 5,665,122 A | 9/1997 | Kambin |
| 5,667,506 A | 9/1997 | Sutterlin |
| 5,667,507 A | 9/1997 | Corin et al. |
| 5,667,508 A | 9/1997 | Errico et al. |
| 5,668,288 A | 9/1997 | Storey et al. |
| 5,669,909 A | 9/1997 | Zdeblick et al. |
| 5,669,910 A | 9/1997 | Korhonen et al. |
| 5,669,911 A | 9/1997 | Errico et al. |
| 5,671,695 A | 9/1997 | Schroeder |
| 5,672,175 A | 9/1997 | Martin |
| 5,674,222 A | 10/1997 | Berger et al. |
| 5,674,295 A | 10/1997 | Ray et al. |
| 5,674,296 A | 10/1997 | Bryan et al. |
| 5,676,665 A | 10/1997 | Bryan |
| 5,676,666 A | 10/1997 | Oxland et al. |
| 5,676,701 A | 10/1997 | Yuan et al. |
| 5,676,703 A | 10/1997 | Gelbard |
| 5,681,311 A | 10/1997 | Foley et al. |
| 5,681,312 A | 10/1997 | Yuan et al. |
| 5,683,391 A | 11/1997 | Boyd |
| 5,683,392 A | 11/1997 | Richelsoph et al. |
| 5,683,393 A | 11/1997 | Ralph |
| 5,683,394 A | 11/1997 | Rinner |
| 5,688,272 A | 11/1997 | Montague et al. |
| 5,688,273 A | 11/1997 | Errico et al. |
| 5,688,274 A | 11/1997 | Errico et al. |
| 5,688,279 A | 11/1997 | McNulty et al. |
| 5,688,280 A | 11/1997 | Booth, Jr. et al. |
| 5,690,629 A | 11/1997 | Asher et al. |
| 5,690,630 A | 11/1997 | Errico et al. |
| 5,690,631 A | 11/1997 | Duncan et al. |
| 5,690,632 A | 11/1997 | Schwartz et al. |
| 5,690,633 A | 11/1997 | Taylor et al. |
| 5,690,842 A | 11/1997 | Panchison |
| 5,693,046 A | 12/1997 | Songer et al. |
| 5,693,053 A | 12/1997 | Estes |
| 5,693,100 A | 12/1997 | Pisharodi |
| 5,697,929 A | 12/1997 | Mellinger |
| 5,697,977 A | 12/1997 | Pisharodi |
| 5,700,291 A | 12/1997 | Kuslich et al. |
| 5,700,292 A | 12/1997 | Margulies |
| 5,702,391 A | 12/1997 | Lin |
| 5,702,392 A | 12/1997 | Wu et al. |
| 5,702,393 A | 12/1997 | Pfaifer |
| 5,702,394 A | 12/1997 | Henry et al. |
| 5,702,395 A | 12/1997 | Hopf |
| 5,702,396 A | 12/1997 | Hoenig et al. |
| 5,702,399 A | 12/1997 | Kilpela et al. |
| 5,702,449 A | 12/1997 | McKay |
| 5,702,450 A | 12/1997 | Bisserie |
| 5,702,451 A | 12/1997 | Biedermann et al. |
| 5,702,452 A | 12/1997 | Argenson et al. |
| 5,702,453 A | 12/1997 | Rabbe et al. |
| 5,702,454 A | 12/1997 | Baumgartner |
| 5,702,455 A | 12/1997 | Saggar |
| 5,704,936 A | 1/1998 | Mazel |
| 5,704,937 A | 1/1998 | Martin |
| 5,707,372 A | 1/1998 | Errico |
| 5,709,681 A | 1/1998 | Pennig |
| 5,709,682 A | 1/1998 | Medoff |
| 5,709,683 A | 1/1998 | Bagby |
| 5,709,684 A | 1/1998 | Errico et al. |
| 5,709,685 A | 1/1998 | Dombrowski et al. |
| 5,709,686 A | 1/1998 | Talos et al. |
| 5,713,841 A | 2/1998 | Graham |
| 5,713,898 A | 2/1998 | Stucker et al. |
| 5,713,899 A | 2/1998 | Marnay et al. |
| 5,713,900 A | 2/1998 | Benzel et al. |
| 5,713,903 A | 2/1998 | Sander et al. |
| 5,713,904 A | 2/1998 | Errico et al. |
| 5,716,355 A | 2/1998 | Jackson |
| 5,716,356 A | | 2/1998 | Biedermann et al. | |
|---|---|---|---|---|
| 5,716,357 A | | 2/1998 | Rogozinski | |
| 5,716,358 A | | 2/1998 | Ochoa | |
| 5,716,359 A | | 2/1998 | Ojima et al. | |
| 5,716,415 A | | 2/1998 | Steffee | |
| 5,716,416 A | | 2/1998 | Lin | |
| 5,720,746 A | | 2/1998 | Soubeiran | |
| 5,720,747 A | | 2/1998 | Burke | |
| 5,720,748 A | | 2/1998 | Kuslich et al. | |
| 5,720,751 A | | 2/1998 | Jackson | |
| 5,722,977 A | | 3/1998 | Wilhelmy | |
| 5,735,853 A | * | 4/1998 | Olerud | 606/71 |
| 5,807,396 A | * | 9/1998 | Raveh | 606/69 |
| 5,954,722 A | * | 9/1999 | Bono | 606/61 |

OTHER PUBLICATIONS

Dickman Curtis A., et al., BNI Quarterly Publication entitled, "Techniques of Screw Fixation of the Cervical Spine," vol. 9, No. 4, Fall 1993, pp. 27–39.

Slone et al., RadioGraphics Publication entitled, "Spinal Fixation," vol. 13, Mar. 1993, pp. 341–356.

Synthes Spine Publication entitled, "The Universal Spinal System—Internal Fixation for the Spine," 1994, pp. 1–15.

AcroMed Publication entitled, "The ISOLA Spinal System—Versatility, simplicity and minimal profile in the surgical treatment of the spine," 1994, pp. 1–15.

AcroMed Corporation Publication entitled, "ISOLA® Transverse Rod Connectors: Principles and Techniques," Date Unknown, pp. i, ii, 1–8.

DANEK Publication entitled, "AXIS—Fixation System," 1993, pp. 1–6.

Synthes Publication entitled, "Small Notched Titanium Reconstruction Plate System," 1996, pp. 1–6.

J. Neurosurg Publication entitled, "Posterior plates in the management of cervical instablility: longterm results in 44 patients," vol. 81, 1994, pp. 341–349.

BNI Quarterly Publication entitled, "Lateral Mass Posterior Plating and Facet Fusion for Cervical Spine Instability," vol. 7, No. 2, 1991, pp. i, ii, 1–12.

Beadling, Lee, Orthopedics Today Publication entitled, "FDA Clears Spinal Cages for Interbody Lumbar Fusion," pp. 1–2.

MedPro Month Publication entitled, "Trends in Spine & Disk Surgery," vol. VI, No. 11–12, pp. 280–284.

Surgical Dynamics Ray Threaded Fusion Cage Device Surgical Technique Manual, pp. 1–10.

Surgical Dynamics Ray Threaded Fusion Cage, pp. 1–6.

AcroMed Publication entitled, "AcroMed Spinal Solutions for Cervical Pathologies," 07–95, pp. 1–8.

Codman Publication entitled, "Sof'wire Cable System," 6 pp.

Huhn, Stephen L. et al., 9"Posterior Spinal Osteosynthesis for Cervical Fracture/Dislocation using a Flexible Multi-strand Cable System: Technical Note," Neurosurgery, vol. 29, No. 6, 1991, pp. 943–946.

Dickman, Curtis A. et al., "Wire Fixation for the Cervical Spine: Biomechanical Principles and Surgical Techniques," BNI Quarterly, vol. 9, No. 4, Fall 1993, pp. 2–16.

Publication by AcroMed entitled, "ACROMED Cable System by Songer," 9/93, 4 pp.

M. Aebi, MD, et al., "Treatment of Cervical Spine Injuries with Anteriro Plating: Indications, Techniques, and Results," vol. 16, No. 3S, Mar., 1991 Supplement, pp. S38–S45.

Foley, M.D. et al., "Aline Anterior Cervical Plating System," Smith & Nephew Richards, Inc. Orthopaedics Catalog Information, Sep. 1996, pp. 1–16.

Lowery, Gary L., M.D., Ph.D., Sofamor Danek Group, Inc. Publication entitled, "Orion Anterior Cervical Plate System: Surgical Technique,"1994, pp. 1–24.

Apfelbaum, R., M.D., Aesculap Scientific Information publication entitled, "Posteriro Transarticular C1–2 Screw Fixation for Atlantoaxial Instability," 1993, pp. 1–15.

Danek Titanium Cable System publication by Danek Group, Inc., 1994, 6 pp.

Publication entitled, "Spinal Disorders", 4 pp.

O'Brien, John P., Ph.D., Orthopaedic Product News Article entitled, "Interbody Fusion of the Lumbar Spine," pp. 1–3.

Roy et al., "Variation of Young's Modulus and Hardness in Human Lumbar Vertebrae Measured by Nanoindentation", pp. 1–4.

Sofamor Anek publication entitled, "Atlas Cable System: Evolution of the Cable System for Spinal Applications," 1995, 2 pp.

AcroMed publication entitled, "AcroMed Songer Cable System: Ordering information for Implants and Instrument," 4/96, 4 pp.

Songer, Matthew, M.D., "Acromed Cable System by Songer: Cervical Technique Manual," pp. 1–17.

Songer, Matthew N., M.D., "ACROMED Cable System by Songer: Technique Manual," 1993, pp. 1–20.

Oxland, Thomas R., Ph.D., et al., SpineTech Inc. Publication entitled, "Biomechanical Rationale—The BAK Interbody Fusion System: An Innovative Solution," pp. 1–16.

Spine Tech, Inc. publication entitled, "Patient Information on Spinal Fusion Surgery and the BAK Interbody Fusion System," 10 pp.

SpineTech, Inc. publication entitled, "BAK/Cervical Interbody Fusion System," 1994, 2 pp.

SpineTech, Inc. publications entitled, "Instrumentation BAK Interbody Fusion System," "Biomechanics BAK Interbody Fusion System," and "Porosity BAK Interbody Fusion System," 1996, 12 pp.

Spine Tech, Inc. publication entitled, "The BAK Interbody Fusion System," 1996, 4 pp.

Depuy Motech, Inc. publication entitled, "Moss Miami 3–Dimensional Spinal Instrumentation: Taking Spinal Instrumentation to a New Dimension," 1995, 8 pp.

Shufflebarger, Harry L., M.D., "Moss Miami Spinal Instrumentaion System: Methods of Fixation of the Spondylopelvic Junction," *Lumbosacral and Spinopelvic Fixation*, 1996 by Raven Publishers, Philadelphia, pp. 381–393.

Shufflebarger, Harry L., M.D. Depuy Motech publication entitled, "Clinical Issue: Rod Rotation in Scoliosis Surgery," 5 pp.

SpineTech, Inc. publication entitled, "The Bone Harvester," 1996, 2 pp.

Wright Medical Technology Publication entitled, "Versalok Low Back Fixation System," 1996, pp. 1–4.

Danek Medical, Inc. Publication entitled, "TSRH Lumbar System," 1991, pp. 1–4.

Spinal Concepts Inc. publication entitled "The BacFix ss—Posterior Lower Fixation System—Written Surgical Technique," 1997, pp. 1–11.

* cited by examiner

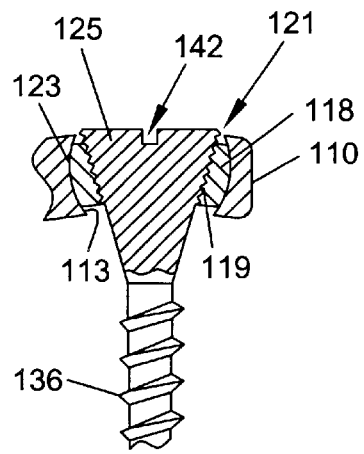
FIG. 9
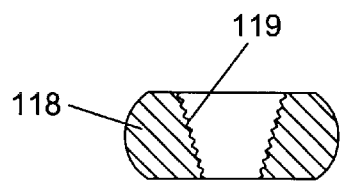   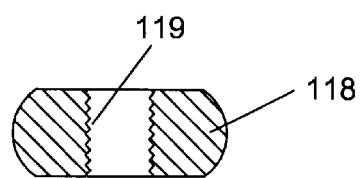
FIG. 10A          FIG. 10B
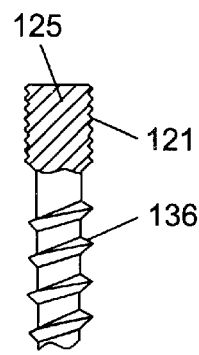   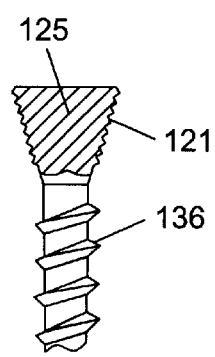
FIG. 11A          FIG. 11B

SYSTEM AND METHOD FOR STABILIZING THE HUMAN SPINE WITH A BONE PLATE

CROSS REFERENCE TO RELATED APPLICATIONS

This application is a continuation-in-part of U.S. patent application Ser. No. 08/905,823, filed Aug. 4, 1997 now abandoned.

BACKGROUND OF THE INVENTION

1. Field of the Invention

The present invention generally relates to spinal fixation systems and the like. More particularly, the present invention generally relates to a spinal plate system that includes a mechanism for fixably attaching screws to a plate.

2. Description of the Related Art

The use of spinal fixation plates for correction of spinal deformities and for fusion of vertebrae is well known. Typically, a rigid plate is positioned to span bones or bone segments that need to be immobilized with respect to one another. Bone screws may be used to fasten the plate to the bones. Spinal plating systems are commonly used to correct problems in the lumbar and cervical portions of the spine, and are often installed posterior or anterior to the spine.

Spinal plate fixation to the cervical portion of the spine can be risky because complications during surgery can cause injury to vital organs, such as the brain stem or the spinal cord. When attaching a fixation plate to a bone, bone screws are placed either bi-cortically (i.e., entirely through the vertebrae such that a portion of the screw extends into the spinal cord region) or uni-cortically (i.e., the screw extends into but not through the vertebrae). Uni-cortical positioning of bone screws has grown in popularity because it is generally safer to use. Bi-cortical screws are intended to breach the distal cortex for maximum anchorage into the bone; however, this placement of the screws may place distal soft tissue structures at risk. Screw placement is of particular importance in anterior cervical plate procedures because of the presence of the spinal cord opposite the distal cortex. Unfortunately, because of the soft texture of the bone marrow, uni-cortical screws may undergo movement from their desired positions. In fact, the portion of the bone surrounding such screws may fail to maintain the screws in their proper positions, resulting in screw backout.

Screw backout is particularly a problem when a pair of screws are implanted perpendicular to the plate. When the screws are placed in such a manner, screw backout may occur as a result of bone failure over a region that is the size of the outer diameter of the screw threads. To overcome this problem, a different configuration of the screws has been developed in which two screws are angled in converging or diverging directions within the bone. Advantageously, the amount of bone that is required to fail before screw backout can occur is increased by this configuration as compared to screws which are implanted in parallel. Although positioning screws angled toward or away from each other in a bone reduces the risk of a screw backout, such backouts can still happen. The result of a screw backout can be damaging to internal tissue structures such as the esophagus because a dislocated screw may penetrate the surface of such structures.

In an attempt to reduce the risk of damage to internal tissue structures, some cervical screw plate systems have been devised in which uni-cortical screws are attached to the plate and not just the bone. It is intended that if screw backout occurs, the screw will remain connected to the plate so that it cannot easily contact internal tissue structures. One such system is described in U.S. Pat. No. 5,364,399 to Lowery et al. and is incorporated by reference as if fully set forth herein. This plating system includes a locking screw at each end of the plate which engages the heads of the bone screws to trap them within recesses of the plate. Since the locking screw is positioned over portions of the bone screws, it may extend above the upper surface of the plate. Thus, the locking screw may come into contact with internal tissue structures, such as the esophagus. Unfortunately, breaches to the esophageal wall may permit bacterial contamination of surrounding tissues, including the critical nerves in and around the spinal cord, which can be fatal.

Another plating system that includes a screw to plate locking mechanism is the Aline™ Anterior Cervical Plating System sold by Smith & Nephew Richards Inc. in Memphis, Tenn. A description of this system can be found in the Aline™ Anterior Cervical Plating System Surgical Technique Manual by Foley, K. T. et al., available from Smith & Nephew Richards Inc., September 1996, pp. 1–16 and is incorporated by reference as if fully set forth herein. The bone screws of this system have openings within each bone screw head for receiving a lock screw coaxially therein. Each bone screw may be inserted into a bone such that the head of the screw is positioned within a borehole of a plate placed adjacent to the bone. The head of each bone screw is slotted such that portions of the head may be deflected toward the plate during insertion of the lock screw within the opening of the bone screw. The bone screw may be thusly locked against the plate. Inserting the lock screw into and fixably positioning the lock screw within the opening may be difficult since the lock screw is very small. The surgeon may be unable to hold onto the lock screw without dropping it. Unfortunately, once such a screw falls into the surgical wound, it is typically difficult to retrieve. In some instances it may be unretrievable.

SUMMARY OF THE INVENTION

An embodiment of the invention relates to an implant system for fixation of the human spine that includes a plate having end boreholes, midline boreholes, screws, and expandable/contractible rings.

The end boreholes preferably extend from the upper surface to the lower surface of the plate. The end boreholes may be disposed in pairs at opposite ends of the plate. Each end borehole is preferably sized to receive at least a portion of a head of a screw therein. Herein, "screw" is taken to mean any elongated member, threaded or non-threaded which is securable within a bone. Each end borehole is also preferably spherical shaped to permit the screw to be "obliquely angulated" relative to the plate. Herein, "obliquely angulated" is taken to mean that the screw may be positioned at a wide range of angles relative to the plate, wherein the range of angles is preferably from 0 degrees to about 15 degrees from an imaginary axis that is perpendicular to the plate. Since the screws may be obliquely angulated with respect to the plate, the occurrence of screw backout from a bone may be significantly reduced.

The expandable/contractible rings are preferably sized so that they may be positioned within each borehole between the plate and each of the screw heads. The inner surface of each ring is preferably shaped to mate with a screw head while the outer surface is preferably shaped to mate with the plate. The outer surface of each screw head may be tapered such that an upper portion of the head is larger than a lower portion of the head. Each ring may also have a gap that extends vertically through the ring to render it expandable/contractible. Thus, during insertion of a screw head within a bone, the ring preferably exerts a compressive force on the screw head to fixably connect the screw to the plate. The screw may be prevented from contacting tissue structures that are protected by the spine even when screw backout occurs since the screw is attached to the plate.

The midline boreholes may be formed through the plate at various locations along a midline axis extending across the plate. The surface of the plate that surrounds each midline borehole is preferably tapered. Further, the heads of screws that may be positioned within the plates preferably have tapered outer surfaces that are shaped to mate with the tapered surface of the plate. Thus, when such a screw head is inserted into a midline borehole, the shape of the plate causes the screw to become fixably attached to the plate in a position that is substantially perpendicular to the plate. Since the midline boreholes may be used when inserting screws into bone graft, oblique angulation of screws positioned within the midline boreholes is not required.

Prior to surgical implantation of the spinal plate system, the expandable/contractible rings may be placed within the end boreholes of the plate. The plate may then be positioned adjacent to a portion of the spine that requires spinal fixation. Holes may be drilled and tapped into a portion of the bone underlying each end borehole at the desired angle. Screws may be inserted through the end boreholes into the holes, and the heads of the screws may be positioned within the boreholes such that the rings surround at least a portion of the heads. Advantageously, during insertion of the screws, the rings preferably lock the screws in place without occupying regions outside of the boreholes. Further, since the rings are pre-positioned within the end boreholes, surgeons do not have to worry that they may drop the rings during insertion of the screws.

In another embodiment, the head is preferably screwed into the ring to create a fixed connection between bone screw and plate at a selected angle. The screw head preferably contains head threading on its outer surface that is complementary to ring threading contained on the inner surface of the ring. The head threading preferably mates with the ring threading to enhance the connection between the bone screw and the ring. The head preferably has a cavity formed on its upper surface for receiving a driving tool such as a screw driver or an alien wrench.

The outer surface of the head is preferably tapered so that screwing the head into the ring causes a change in width of the ring to fix the bone screw in position relative to the plate. The inner surface of the ring may also be tapered to substantially match the taper on the outer surface of the head. At least a portion of the head preferably has a width greater than the inner width of the ring. As the screw head is screwed into the ring, the ring preferably expands outwardly from its inner surface to accommodate the increasing width of the screw head. The ring may contain one or more slots or gaps as previously described to facilitate expansion of the ring against the inner surface of the borehole.

It is believed that using a threading engagement between the head and ring increases the hoop stress exerted on the head, resulting in a stronger connection between the bone screw and the plate. Moreover, if bone threading becomes loose within a bone, screw backout from plate will tend to be resisted by the threaded connection between the screw head and the ring. Thus, even if the shank loosens within the bone, the head will tend to remain within the borehole of the plate so as not to protrude from the plate into surrounding body tissue.

BRIEF DESCRIPTION OF THE DRAWINGS

Further advantages of the present invention will become apparent to those skilled in the art with the benefit of the following detailed description of preferred embodiments and upon reference to the accompanying drawings in which:

FIG. 9 is a cross-sectional view of a tapered screwhead connected to a tapered ring through a threaded engagement;

FIG. 10A is a cross-sectional view of a ring having a tapered inner surface;

FIG. 10B is a cross-sectional view of a ring having a non-tapered inner surface;

FIG. 11A is a cross-sectional view of a screw head having a non-tapered outer surface;

FIG. 11B is a cross-sectional view of a screw head having a tapered outer surface;

Figure 1:
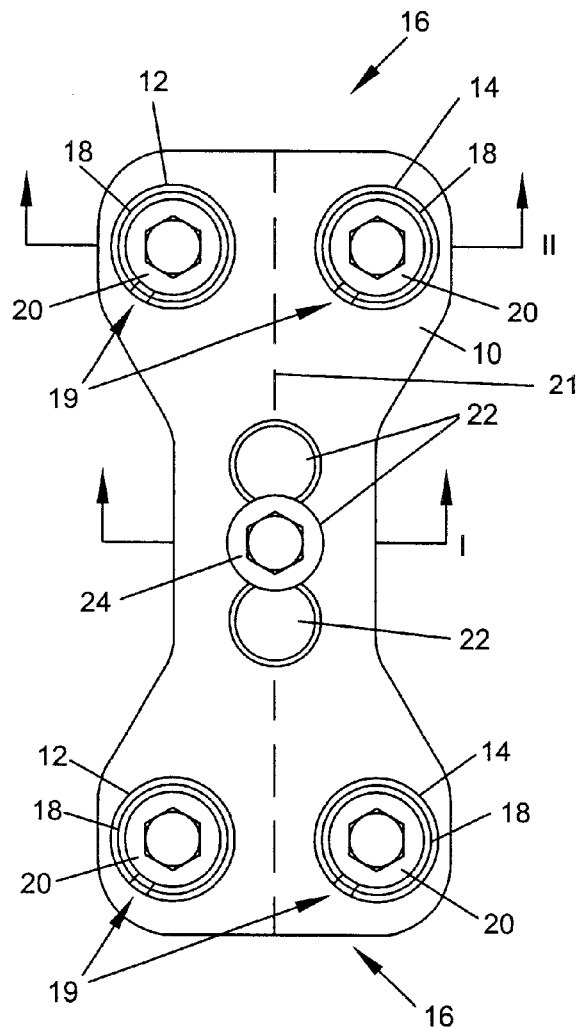
FIG. 1 is a top plan view of one embodiment of a spinal plating system that may be used for fixation of the human spine.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DESCRIPTION OF THE PREFERRED EMBODIMENTS

Turning to FIG. 1, a top plan view of a spinal plating system is depicted according to an embodiment of the present invention. The spinal plating system may be used to correct problems in the lumbar and cervical portions of the spine. For example, the plating system may be implanted into the occiput bone which is located at the base of the skull. The plating system is preferably installed anterior to the spine. The spinal plating system preferably includes a plate 10 that may be placed adjacent to a portion of the spine. The length of plate 10 is preferably chosen so that the plate may span between at least two vertebrae. Plate 10 preferably includes two pairs of end boreholes 12 and 14, located at opposite ends 16 of plate 10. End boreholes 12 and 14 are preferably formed vertically through plate 10 such that they extend from an upper surface to a lower surface of the plate. End boreholes 12 and 14 are preferably spaced from a longitudinal midline axis 21 of plate 10 by the same distance.

End boreholes 12 and 14 are preferably shaped to receive the heads of bone screws 20 during spinal implantation. The spinal plating system further includes rings 18 that may be disposed within each of the end boreholes 12 and 14 for fixedly attaching bone screws 20 to plate 10. A gap 19 preferably exists in each of the rings. 18 to enable the rings to contract or expand under pressure. The spinal plating system may also include one or more midline boreholes 22 that extend vertically through plate 10 at some point along the midline axis 21 of plate 10. Preferably, one of the midline boreholes 22 is located at the middle of plate 10 while other midline boreholes are offset from the middle. The head of screw 24 may be positioned within one of the midline boreholes 22. This configuration of midline boreholes 22 may provide a surgeon with more options as to the location of a screw 24 so that the screw may be placed in the most desirable location. Such a screw 24 may be used to connect plate 10 to bone graft. Those elements that make up the spinal plating system are preferably composed of steel (e.g, stainless steel), pure titanium, steel alloys or titanium alloys because such materials are generally nontoxic, biocompatible, strong, and non-corrosive. Other materials which have these properties may also be used to form the elements.

Figure 2:
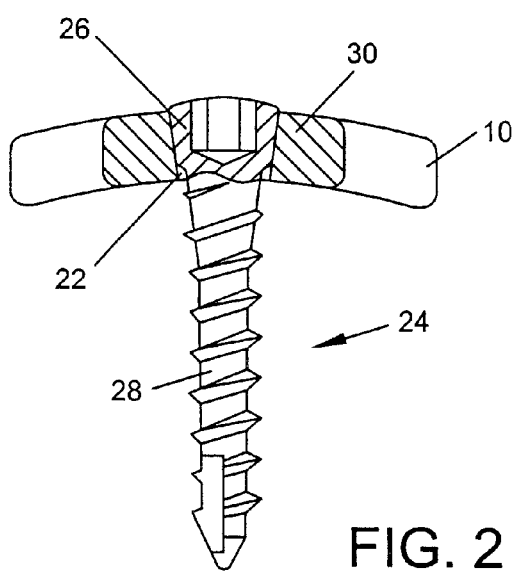
FIG. 2 is a cross-sectional view of the spinal plating system along plane I of FIG. 1.

FIG. 2 illustrates a cross-sectional view of the spinal fixation system along plane I of FIG. 1. Particularly, FIG. 2 shows how screw 24 is attached to plate 10 within one of the midline boreholes 22. Screw 24 preferably includes a head 26 and a shank 28 that extends from the base of head 26. The inner surface of a portion 30 of plate 10 that surrounds borehole 22 is preferably tapered, making borehole 22 larger at the top than at the bottom. The outer surface of head 26 is also preferably tapered so that head 26 may fit snugly within borehole 22. In fact, the shape of plate 10 and head 26 preferably promotes attachment of screw 24 to plate 10. During implantation of screw 24 into bone graft, the shank of the screw is preferably screwed into a hole that has been formed in the bone graft underlying borehole 22. Because the bottom portion of borehole 22 is smaller than the upper portion of the screw head 26, screw 24 may become locked into place within borehole 22 once it has been screwed to a desired depth within the bone graft. The plate is also shown as having a slight curvature to enhance its fixation to the spine.

Figure 3:
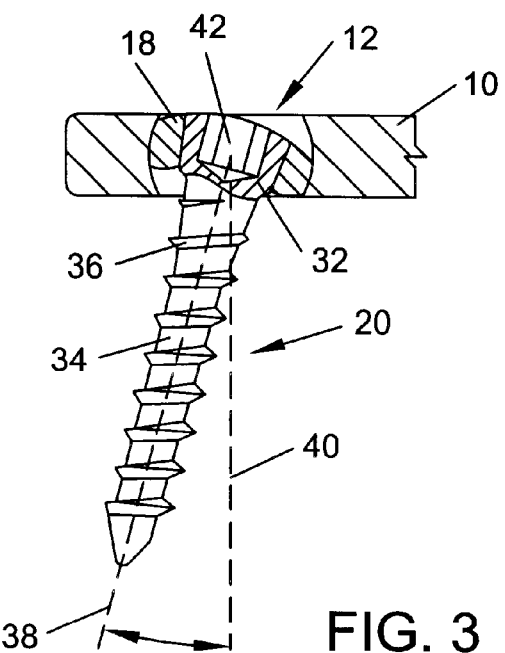
FIG. 3 is a cross-sectional view of a screw within an end borehole of a plate, wherein the screw is positioned according to one embodiment of the present invention.

FIG. 3 depicts a cross-sectional view of an embodiment of one of the end boreholes 12 and 14 in which screw 20 is disposed. Borehole 12 is preferably substantially arcuate or spherical in shape so that a head 32 of screw 20 may be rotated and moved to various positions within borehole 12. Ring 18 is preferably sized to fit into borehole 12 between plate 10 and head 32. The outer surface of ring 18 is preferably curved to permit movement of the ring within borehole 12. The combination of ring 18 and borehole 12 is like that of a ball and socket since ring 18 may be rotated both horizontally and vertically in clockwise and counter-clockwise directions within borehole 12. Ring 18 may also be rotated in directions that are angled away from the horizontal and vertical directions. In FIG. 3, ring 18 at least partially surrounds head 32 of screw 20 which is positioned within borehole 12. A shank 34 of bone screw 20 preferably has threading 36 to allow the screw to be inserted into a bone when screw 20 is rotated in a clockwise direction. Head 32 preferably includes a cavity 42 that extends from the top of the head to an inner portion of the head. Cavity 42 may be shaped to receive the end of any fastening device e.g., a hexagonal wrench, that may be used to turn screw 20.

Figure 4:
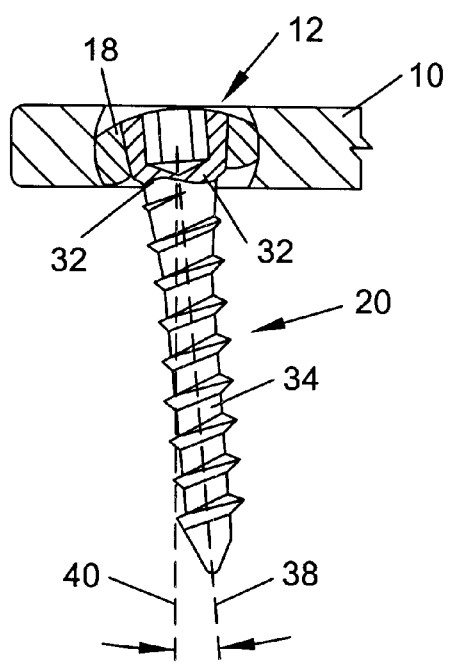
FIG. 4 is a cross-sectional view of the screw, wherein the screw is positioned according to another embodiment.

Screw 20 may be simultaneously screwed into a bone and moved to its desired position. The inner surface of ring 18 and the outer surface of head 32 are preferably tapered and shaped to mate with each other. The bottom portion of head 32 is preferably smaller than the upper portion of ring 18. As screw 20 is inserted into a bone, head 32 preferably applies a radial force to ring 18, thereby causing the ring to expand within the borehole and increase the size of gap 19. An interference fit may form between screw head 32, ring 18, and plate 10 in which these elements fit so tightly together that they obstruct the movements of each other. The hoop stress of ring 18 on head 32 may fixedly attach screw 20 to plate 10. Also, during insertion of screw 20, screw head 32 and ring 18 may be positioned within borehole 12 such that their left sides are at a higher elevation than their right sides (or vice versa). FIG. 3 shows that positioning screw head 32 in this configuration may result in a centerline 38 of shank 34 being obliquely angulated with respect to plate 10. In fact, centerline 38 may be positioned where it is at an angle ranging from 0 to 15 degrees with respect to an imaginary axis 40 which is perpendicular to plate 10. FIG. 3 demonstrates shank 34 of screw 20 being angled to the left of imaginary axis 40 while FIG. 4 demonstrates shank 34 being angled to the right of imaginary axis 40. Screw 20 is not limited to these positions and can be angled in various directions, such as into the page.

Figure 5:
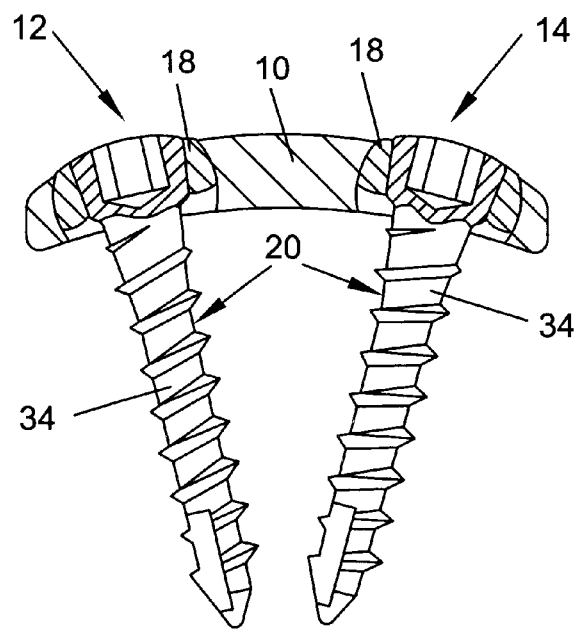
FIG. 5 is a cross-sectional view of the spinal plating system along plane II of FIG. 1, wherein a pair of screws extend in converging directions, according to one embodiment.
Figure 6:
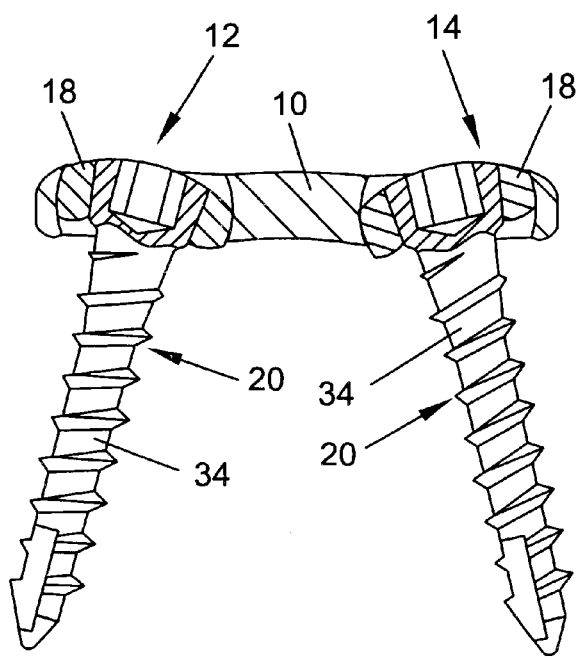
FIG. 6 is a cross-sectional view of the spinal plating system along plane II of FIG. 1, wherein the pair of screws extend in diverging directions, according to another embodiment.

FIG. 5 and FIG. 6 depict different embodiments of the spinal plating system along plane II of FIG. 1. FIG. 5 shows that screws 20 may be positioned within end boreholes 12 and 14 such that they extend in converging directions with respect to each other. The screws 20 depicted in FIG. 6 are shown as being positioned such that their shanks 34 extend in diverging directions with respect to each other. Screws 20 may be moved to such positions as described above. Screws 20 may also be moved to positions such that the screws are non-planar with respect to a latitudinal plane extending through plate 10. For example one screw 20 may be positioned out of the page and the other screw 20 may be positioned into the page. Since bone screws 20 may be placed in diverging or converging directions through end boreholes 12 and 14 at both ends of plate 10, screw backout may be greatly reduced. Further, the use of rings 18 to fixedly attach screws 20 to plate 10 may prevent damage to tissue structures by any screws that are able to escape from the bone. Rings 18 preferably do not extend above the upper surface of plate 10, and thus advantageously do not contact tissue structures. Screw 20 may be placed in a uni-cortical position within the bone since the problem of screw backout is greatly reduced by the diverging or converging screw configurations.

According to one embodiment, the spinal fixation system of FIG. 1 is prepared for surgical implantation by pre-positioning of rings 18 within end boreholes 12 and 14. During the actual surgical procedure, holes may be drilled and tapped into the bones to which plate 10 is to be attached. Plate 10 may then be positioned adjacent to the bones. Each of the screws 20 may be screwed into the bone holes while they are being positioned within their corresponding boreholes 12 and 14. Each pair of screws 20 at opposite ends 16 of plate 10 are preferably moved to positions where they are at an oblique angle relative to the plate. The insertion force of each screw 20 into each ring 18 preferably causes the ring to exert a compressive force on the screw head, thereby fixably connecting the screws to plate 10. If necessary, screw 24 may be positioned in one of the midline boreholes 22 such that screw 24 becomes fixedly attached to plate 10.

Each of the features of the embodiments discussed above may be combined or used individually.

FURTHER IMPROVEMENTS

The following additional embodiments may be used individually or in combination with any of the embodiments described above.

Figure 7:
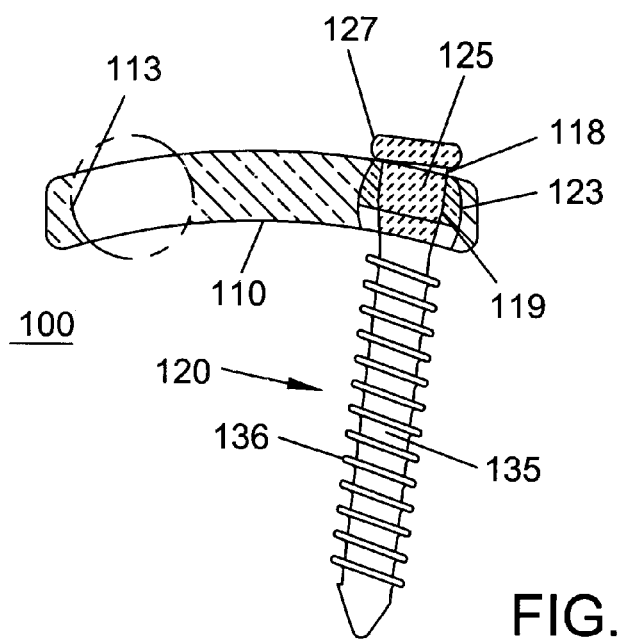
FIG. 7 is a side view in partial cross-section of a spinal fixation system that includes a screw, a ring, and a plate.

A side view of an embodiment of a spinal plate system 100 is shown in FIG. 7. Spinal plate system 100 preferably includes a bone screw 120, a ring 118, and bone plate 110. Plate 110 may be used to stabilized a bony structure such as the spine to facilitate a bone fusion (e.g., a spinal fusion). The bone screw 120 may be used to connect plate 110 to a bone such as a vertebra. Ring 118 preferably fixes bone screw 120 to plate 110 at a selected angle that depends upon the patient's anatomy. Bone screw 120, ring 118, and bone plate 110 are preferably capable of being used in similar applications as screw 20, ring 18, and plate 10 as previously described in FIGS. 1–6.

Figure 8:
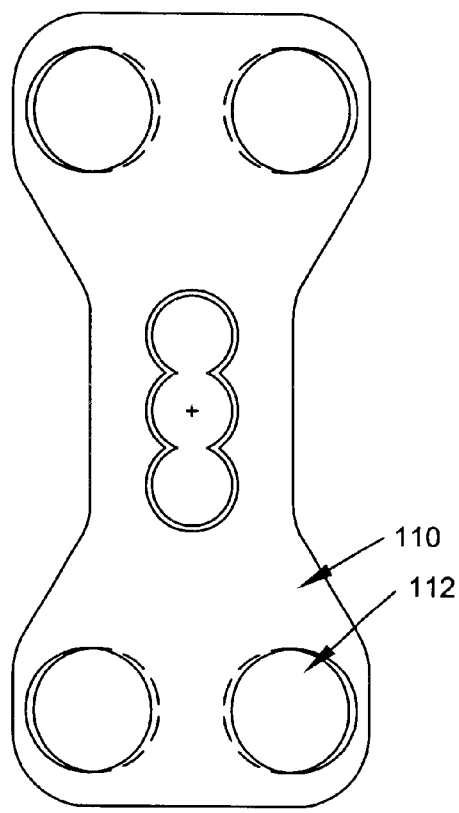
FIG. 8 is a top view of an embodiment of the plate depicted in FIG. 7.

A top view of an embodiment of plate 110 is shown in FIG. 8. Plate 110 preferably includes one or more boreholes 112 and may function similarly to plate 10 as described above. Each borehole 112 preferably has a curvate inner surface 113 (shown in FIG. 7) for engaging the outer surface 123 of ring 118. The inner surface 113 preferably has the shape of a portion of an outer surface of a sphere. Borehole 112 has a width that is defined across the inner surface 113 of the borehole. The width of the borehole may vary in a direction axially through the borehole. In FIG. 7, for example, the width of the boreholes preferably increases from a top surface 102 of the plate to about the middle of the plate. The width of the borehole in FIG. 7 then preferably decreases from about the middle of the plate to a lower surface 104 of the plate such that the borehole has a maximum width near the midpoint between upper surface 102 and lower surface 104 of the plate.

The outer surface 123 of ring 118 is preferably curvate for engaging the inner surface 113 of the borehole. The shape of surfaces 123 and 113 preferably allow ring 118 to swivel within the borehole. The swiveling action may be similar to that of a ball and socket joint. The ring preferably surrounds at least a portion of the head 125 of a bone screw. The enlarged end 127 disposed on head 125 is optional and need not be included if it inhibits angulation of the bone screw. The swiveling of the ring within the borehole preferably enables the shank 135 of the bone screw 120 to rotate in a substantially conical range of motion. In this manner, the head is preferably movable within the borehole, and the shank is adjustably positionable at a plurality of angles substantially oblique to the plate.

In an embodiment, the surfaces 123 and 113 are preferably shaped to provide a conical range of motion to the shank that is within a preferred range of angles. The head is preferably movable within the borehole such that the shank can be positioned at a selected angle relative to an imaginary axis running perpendicular to the plate proximate borehole 112. The selected angle is preferably less than about 45 degrees, more preferably less than about 30 degrees, and more preferably still less than about 15 degrees.

Ring 118 preferably has an outer width that is less than or about equal to the width of borehole 112 at a location between upper surface 102 and lower surface 104 of the plate. In this manner, ring 118 may be positioned within borehole 112 proximate the middle of the borehole to enable the bone screw 120 to extend substantially perpendicularly from the bone plate 110. Prior to surgery, rings 118 are preferably pre-positioned within boreholes 112 of plate 110. "Pre-positioned" is taken to mean that the rings are capable of swiveling within the borehole but are preferably inhibited from falling out of the borehole because of the reduced width of the borehole proximate the upper and lower surfaces. The width of the borehole proximate the upper and lower surfaces of plate 110 is preferably less than or about equal to the outer width of the ring to inhibit the ring from falling out of the borehole. In this manner, the surgeon may use a plate 110 having rings 118 pre-positioned within the boreholes 112 such that the rings will not fall into the surgical wound when spinal system 100 is installed.

Alternately, the rings 118 can be manually positioned within the boreholes during surgery. Ring 118 preferably includes one or more slots or gaps 19 (as shown in FIG. 1). The slot preferable allows the ring to be contracted or expanded. Contraction of ring 118 may allow the ring to be positioned within the borehole during surgery. Once positioned within the borehole the ring preferably expands and is inhibited from falling out of the borehole.

The ring 118 is preferably capable of being swiveled such that one portion of the ring is adjacent to upper surface 102 of plate 110 while another portion of the ring lies adjacent to lower surface 104 of plate 110. The ring is preferably sufficiently thin to allow it to reside within the borehole without extending from the borehole beyond the upper surface 102 or lower surface 104 of the plate. Generally, it is preferred that the ring and screw head remain within the borehole 112 to minimize the profile width of spinal system 100. In some embodiments, however, the bone screw 120 may be capable of being angulated relative to the plate 110 such that the ring 118 extends from the borehole 112 beyond a surface of the plate 110.

The head 125 is preferably screwed into ring 118 to create a fixed connection between bone screw 120 and plate 110 at a selected angle. In an embodiment depicted in FIG. 9, screw head 125 preferably contains head threading 121 on its outer surface that is complementary to ring threading 119 contained on the inner surface of ring 118. The head threading 121 preferably mates with the ring threading 119 to enhance the connection between the bone screw 120 and the ring 118. The head 125 preferably has a cavity 142 formed on its upper surface for receiving a driving tool such as a screw driver or an allen wrench.

The outer surface of the head 125 is preferably tapered so that screwing the head into the ring causes a change in width (e.g., expansion) of the ring 118 to fix the bone screw 120 in position relative to the plate 110. The inner surface of the ring 118 may also be tapered to substantially match the taper on the outer surface of the head. At least a portion of the head 125 preferably has a width greater than the inner width of the ring 118. As the screw head is screwed into the ring 118, the ring preferably expands outwardly from its inner surface to accommodate the increasing width of the screw head 125. The ring 118 may contain a slot or gap 19 (as shown in FIG. 1) as previously described to facilitate expansion of the ring against the inner surface 113 of the borehole 112. The slot is preferably widened as a result of force received from head 125. The force exerted by head 125 against the inner surface of ring 118 preferably presses the ring into a fixed engagement against inner surface 113 of borehole 112.

Figure 12:
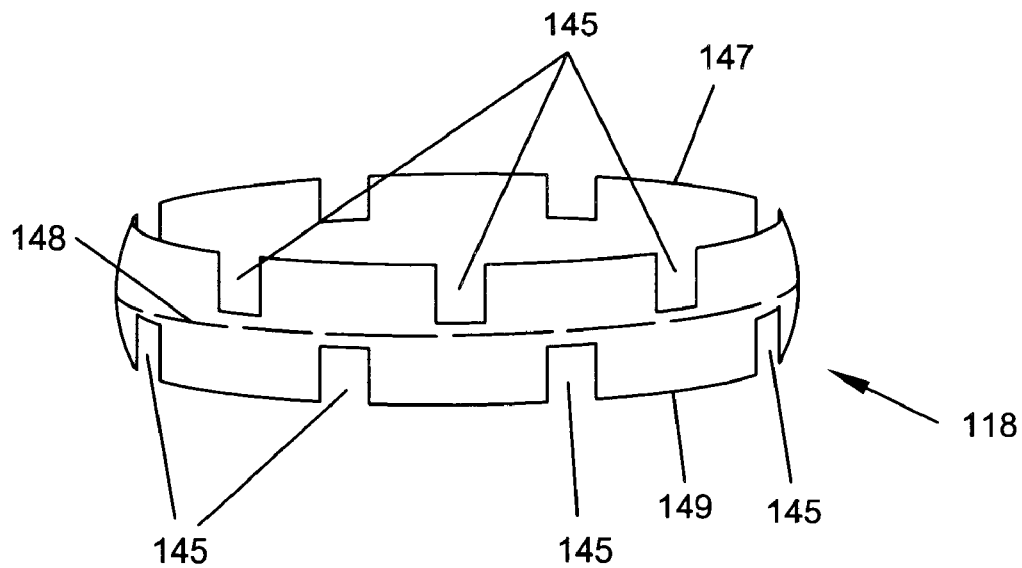
FIG. 12 is a side view of a ring having a plurality of slots.

Alternatively, ring 118 may contain one or more partial slots 145, as depicted in FIG. 12. Each partial slot 145 preferably extends from a top 147 or bottom 149 of ring 118 into the ring. Partial slots may extend up to about midpoint 148 of ring 118. In one embodiment, a plurality of slots 145 may be oriented about the ring such that alternate slots extend from the top 147 and/or the bottom 149 of ring 118, as depicted in FIG. 12. These alternating partial slots preferably facilitate the expansion and contraction of ring 118.

Cross-sectional views of two embodiments of ring 118 are shown in FIGS. 10A and 10B. The ring may contain an inner surface that is tapered (as shown in FIG. 10A) or that is substantially untapered (as shown in FIG. 10B). Cross sectional views of two embodiments of screw 120 are shown in FIGS. 11A and 11B. The head 125 may have a substantially untapered outer surface (as shown in FIG. 11A) or a substantially tapered outer surface (as shown in FIG. 11B). It is to be understood that each of the heads of the screws depicted in FIGS. 11A and 11B may be used in combination with either of the rings 118 depicted in FIG. 10A or FIG. 10B. It is also to be appreciated that the head of the screw may include an outer surface having a substantially untapered portion along with a tapered portion proximate its end for expanding the ring 118.

As described herein, a "ring" is taken to mean any member capable of fitting between the inner surface 113 borehole and the bone screw 120 to connect the bone screw to the bone plate 110. The ring is preferably substantially circular to surround head 125, but the ring may instead have a non-circular shape. The ring may be made of a number of biocompatible materials including metals, plastics, and composites.

It is believed that using a threading engagement between the head 125 and ring 118 increases the hoop stress exerted on head 125, resulting in a stronger connection between the bone screw 120 and the plate 110. Moreover, if bone threading 136 becomes loose within a bone, screw backout from plate 110 will tend to be resisted by the threaded connection between the screw head 125 and the ring 118. Thus, even if the shank 135 loosens within the bone, the head will tend to remain within the borehole of the plate so as not to protrude from the plate into surrounding body tissue.

As shown in FIG. 9, the head threading 121 on the head 125 and the ring threading 119 on the inner surface of ring 118 is preferably substantially fine relative to the threading 136 on bone screw 120. That is, the pitch of the head threading 121 and ring threading 119 is preferably smaller than that on bone screw 120. The ring threading 119 preferably has multiple starts to facilitate connection of the bone screw and the ring. In one embodiment the ring threading 119 has a double start such that the head can be started into the ring threading at either one of two orientations offset by 180 degrees. In another embodiment, the ring threading has a triple start such that the head can be started into the ring threading at any one of three orientations offset by 120 degrees.

The ring threading 119 and head threading 121 are preferably pitched to a substantially similar degree to the threading 136 on the bone screw 120. Preferably, the ring threading 119 and head threading 121 are pitched such that the head 125 causes expansion of the ring 118 while the bone screw 120 is being inserted into the bone.

During the surgical procedure for attaching the plate 110 to a bone, holes may be drilled and tapped into the bones to which plate 110 is to be attached. Plate 110 may then be positioned adjacent to the bones. A ring 118 may be positioned within the borehole. A bone screw 120 may be positioned through ring 118 such that the head threading 121 of head 125 engages the ring threading 119 of ring 118. The bone screw 120 may then be rotated to insert the bone screw into the bone. As the screw is rotated the head threads and ring threads preferably interact such that the head is moved into the ring. Movement of the head 125 into the ring 118 preferably causes the ring to expand such that the orientation of the bone screw 120 relative to the plate 110 is fixed. Preferably, the ring threading and head threading is pitched such the orientation of the bone screw 120 is fixed after plate 110 engages the bone.

The bone screws may be used in pairs to prevent screw backout. The bone screws are preferably positioned into the bone in substantially converging or substantially diverging directions relative to one another.

Figure 13:
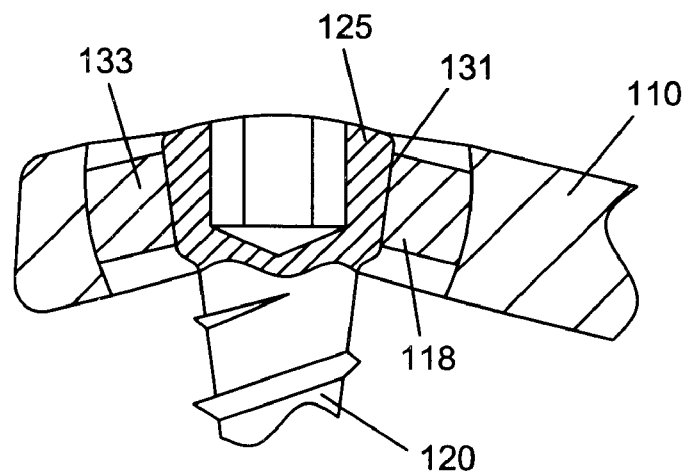
FIG. 13 is a cross-sectional view of a screw head position ed within a ring.

In an embodiment, a stronger connection between the bone screw 120 and the plate 110 may be formed by texturing either outer surface 131 of head 125 of bone screw 120 or inner surface 133 of ring 118, as depicted in FIG. 13. Preferably, both surfaces are textured to inhibit movement of the bone screw with respect to the plate. During typical manufacturing procedures, outer surface 131 of head 125 and inner surface 133 of ring 118 may be formed as relatively smooth surfaces. While the friction between these smooth surfaces tends to be sufficient to maintain bone screw 120 in a fixed position with respect to plate 110, under stressful conditions the bone screw may be forced out of ring 118. By providing at least one textured surface, the coefficient of friction between head 125 of bone screw 120 and ring 118 may be increased. This increase in friction between bone screw 120 and ring 118 may further inhibit screw backout from plate 110.

A number of textured surfaces may be used to increase the coefficient of friction between ring 118 and head 125 of bone screw 120. In general, any process which transforms a relatively smooth surface into a roughened surface having an increased coefficient of friction may be used. Methods for forming a roughened surface include, but are not limited to: sanding, forming grooves within a surface, ball peening processes, electric discharge processes, and embedding of hard particles within a surface.

In one embodiment a plurality of grooves may be formed in outer surface 131 of head 125 of bone screw 120 or inner surface 133 of ring 118. Preferably, a plurality of grooves is formed in both outer surface 131 and inner surface 133. While it is preferred that both outer surface 131 and the inner surface 133 be textured, texturing of only one of the surfaces may be sufficient to attain additional resistance to movement.

In another embodiment, the frictional surface may be created by an electrical discharge process. An electrical discharge process is based on the principle of removal of portions of a metal surface by spark discharges. Typically a spark is generated between the surface to be treated and an electrode by creating potential differential between the tool and the electrode. The spark produced tends to remove a portion of the surface disposed between the electrode and the surface. Typically, the electrode is relatively small such that only small portions of the surface are removed. By moving the electrode about the surface numerous cavities may be formed within the surface. Typically these cavities are somewhat pyramidal in shape. Various patterns may be formed within the surface depending on how the electrode is positioned during the discharge. Electric discharge machines are well known in the art. A method for forming a frictional surface within a metal surface using an electric discharge process is described in U.S. Pat. No. 4,964,641 to Miesch et al. which is incorporated by reference as if set forth herein.

A variety of patterns may be formed using an electric discharge machine. Preferably a diamond pattern or a waffle pattern is formed on either inner surface 133 of ring 118 or outer surface 131 of head 125 of bone screw 120.

In another embodiment, inner surface 131 of ring 118 and/or outer surface 133 of head 125 of bone screw 120 may be textured by the use of a shot peening process. A shot peening process for forming a textured surface is described in U.S. Pat. No. 5,526,664 to Vetter which is incorporated by reference as if set forth herein. In general, a shot peening process involves propelling a stream of hardened balls, typically made of steel, at a relatively high velocity at a surface. To create a pattern upon an area of the surface the stream is typically moved about the surface. The speed by which the stream is moved about the surface tends to determine the type of textured surface formed.

Preferably, the stream is moved such that a pattern resulting in a textured surface having ridges and valleys is formed on inner surface 133 of ring 118 and outer surface 131 of head 125 of bone screw 120. When the textured inner surface 131 of ring 118 and the textured head 125 of bone screw 120 are coupled together the ridges and valleys may interact with each other to provide additional resistance to movement in either a longitudinal direction or a direction perpendicular to the longitudinal axis.

In another embodiment, the textured surface may be produced by embedding sharp hardened particles in the surface. A method for embedding sharp hardened particles in a metal surface is described in U.S. Pat. No. 4,768,787 to Shira which is incorporated by reference as if set forth herein. The method of Shira involves using a laser or other high energy source to heat the surface such that the surface melts in selected areas. Just before the molten area re-solidifies, a stream of abrasive particles is directed to the area. In this manner some of the particles tend to become embedded within the molten surface. The particles typically have a number of sharp edges that protrude from the surface after the particles have been embedded within the surface.

Any of the above methods of texturing may be used in combination with another method. For example, outer surface 131 of head 125 of bone screw 120 may be textured using a pattern of grooves. Inner surface of ring 118, however, may be textured using an electrical discharge method. When coupled together the textured surfaces of bone screw 120 and ring 118 may interact with each other to provide additional resistance to movement in either a longitudinal direction or a direction perpendicular to the longitudinal axis.

Textured surfaces may also be formed on any of the other surfaces of the plate system. The formation of textured surfaces preferably increases the frictional resistance between the various components of the plate system.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A spinal fixation system, comprising:
    a plate for stabilizing a spine, the plate comprising a borehole;
    a bone screw comprising a head and a shank;
    a ring for inhibiting backout of the bone screw from the plate, the ring being positionable within the borehole between the plate and the bone screw during use, and wherein the ring allows the bone screw to be inserted into a bone at a desired angle relative to the plate;
    and wherein the head and the ring are configured to couple together without fixedly engaging the ring to the plate during use.

2. The system of claim 1, wherein the ring is configured to substantially surround the head during use, and wherein rotating the bone screw rotates the ring when the ring and bone screw are coupled together.

3. The system of claim 1, wherein the head comprises an outer threaded surface and the ring comprises an inner threaded surface, wherein the head threading is complementary to the ring threading.

4. The system of claim 3, wherein the ring threading has multiple starts to facilitate connection of the bone screw and the ring during use.

5. The system of claim 3, wherein the ring threading has a double start to facilitate connection of the bone screw and the ring during use.

6. The system of claim 3, wherein the ring threading has a triple start to facilitate connection of the bone screw and the ring during use.

7. The system of claim 3, wherein the shank comprises bone threading having a first pitch, and wherein the ring threading comprises a second pitch, the second pitch being substantially equal to the first pitch.

8. The system of claim 3, wherein the shank comprises bone threading having a first pitch, and wherein the ring threading comprises a second pitch, the second pitch being substantially equal to the first pitch, and wherein the pitch is predetermined to allow the plate to contact the bone when the bone screw is inserted within the bone and coupled to the ring.

9. The system of claim 1, wherein the ring is movable within the borehole such that the shank is rotatable in a substantially conical range of motion to allow the shank to be positioned at a selected angle relative to the plate.

10. The system of claim 1, wherein the ring comprises one or more slots to allow it to expand.

11. The system of claim 1, wherein the ring comprises one or more slots to allow it to contract.

12. The system of claim 1, wherein the borehole comprises an inner surface and a width across the borehole, the inner surface being curved such that the width varies in a direction axially along the borehole.

13. The system of claim 1, wherein the borehole comprises a substantially curvate inner surface, and wherein the ring further comprises a substantially curvate outer surface, the curvate outer surface being shaped to allow the ring to swivel within the borehole.

14. The system of claim 1, wherein the plate comprises an upper surface and lower surface, and wherein the ring comprises an outer surface and an outer ring width, and wherein the borehole comprises a substantially curvate inner surface and a width defined across the inner surface, the width of the borehole varying in a direction axially along the borehole, and wherein the width of the borehole is greater than about the outer ring width at a location between the upper and lower surface, and wherein the width of the borehole is not greater than the outer ring width proximate the upper and lower surfaces.

15. The system of claim 1, wherein the plate comprises an upper surface and a lower surface, and wherein the borehole extends between the upper and lower surfaces, the borehole comprising a width that varies in a direction axially along the borehole, and wherein the ring is disposed within the borehole, the ring further comprising an outer ring width that is greater than about the width of the borehole proximate the upper and lower surfaces, the outer ring width being sized relative to the width of the borehole proximate the upper and lower surfaces to substantially inhibit the ring from being removed from the borehole.

16. The system of claim 1, wherein the ring is configured to reside within the borehole without extending above an upper surface of the plate during use.

17. The system of claim 1, wherein the ring substantially surrounds the head of the bone screw, and wherein the bone screw is capable of being angulated relative to the plate during use such that the head remains below the upper surface of the plate.

18. The system of claim 1, wherein the plate comprises a second borehole, and the system further comprises:
  a second bone screw comprising a second head and a second shank, the head of the second bone screw comprising threading;
  a second ring for coupling the second bone screw to the plate, the second ring being positionable within the second borehole between the plate and the second bone screw during use, the second ring comprising second ring threading for engaging the threading on the head of the second bone screw during use;
  and wherein the shanks of the first bone screw and the second bone screw are positionable to extend into the bone in substantially converging or substantially diverging directions relative to one another during use.

19. The system of claim 18, wherein the first shank is positioned at a first oblique angle relative to the plate during use, and wherein the second shank is positioned at a second oblique angle relative to the plate during use, and wherein the first shank and the second shank extend in diverging directions relative to each other during use.

20. The system of claim 18, wherein the first shank is positioned at a first oblique angle relative to the plate during use, and wherein the second shank is positioned at a second oblique angle relative to the plate during use, and wherein the first shank and the second shank extend in converging directions relative to each other during use.

21. The system of claim 1, wherein the ring is rotatable within the borehole so that the shank is positionable through the ring at a selectable angle that is less than about 15 degrees relative to a plane substantially perpendicular to the plate.

22. The system of claim 1, wherein the ring comprises a plurality of slots extending from a bottom and a top of the ring to a middle portion of the ring.

23. The system of claim 1, wherein the ring further comprises threading, wherein the head further comprises threading, and wherein the ring threading mates with the head threading to couple the ring to the head.

24. The system of claim 1, wherein the ring further comprises a roughened inner surface configured to couple the head to the plate.

25. The system of claim 1, wherein the head further comprises a roughened outer surface configured to couple to an inner surface of the ring.

26. A method for stabilizing a spine, comprising:
  positioning a plate adjacent to a bone, the plate comprising a borehole;
  moving a shank of a bone screw into a ring positioned within the borehole, the bone screw comprising a head having an outer surface with head threading disposed thereon, the ring comprising a substantially curvate outer surface and an inner surface having ring threading disposed thereon that mates with the head threading, the borehole comprising a substantially curvate inner surface;
  angulating the bone screw by swiveling the outer surface of the ring across the inner surface of the borehole to position the bone screw;
  engaging the ring threading with the head threading to couple the ring to the bone screw; and
  advancing the bone screw into the bone to connect the plate to the bone;
  wherein the coupled ring and bone screw are configured to move within the borehole without the ring fixedly engaging the plate during use.

27. The method of claim 26, wherein the bone screw is fixed in a position whereby it extends from the plate at a substantially oblique angle.

28. The method of claim 26, wherein the ring comprises one or more slots, and wherein the slot is widened when the head is moved through the ring.

29. The method of claim 26, further comprising drilling and/or tapping an opening into the bone that is shaped to receive the bone screw prior to advancing the bone screw into the bone.

30. The method of claim 26, further comprising screwing a second bone screw into the bone, the second bone screw extending through a second borehole in the plate such that the two bone screws extend in diverging directions relative to each other.

31. The method of claim 26, further comprising screwing a second bone screw into the bone, the second bone screw extending through a second borehole in the plate such that the two bone screws extend in converging directions relative to each other.

32. The method of claim 26, wherein the ring is movable within the borehole so that the shank of the bone screw that is positioned within the ring before the bone screw is advanced into the bone is rotatable in a substantially conical range of motion relative to the plate.

33. The method of claim 26, wherein the ring threading has multiple starts to facilitate engagement of the ring threading with the head threading.

34. The method of claim 26, further comprising manually inserting the ring within the borehole prior to moving the bone screw through the ring.

35. The method of claim 26, wherein the borehole is shaped to substantially inhibit the ring from being removed from the borehole, and further comprising swiveling the ring about the borehole to position the bone screw.

36. The method of claim 26, wherein the ring does not extend from the borehole beyond a surface of the plate after bone screw is advanced into the bone.

37. The method of claim 26, wherein the ring is movable within the borehole such that the shank of the bone screw is positionable within the ring in a substantially conical range of motion to allow the shank to be positioned at a selected angle of less than about 15 degrees relative to a plane substantially perpendicular to the plate.

38. The system of claim 26, wherein the bone screw and the ring rotate together within the borehole when the ring threading and the head threading are engaged together during use.

39. A spinal fixation system, comprising:
a plate for stabilizing a spine, the plate comprising a borehole;
a ring positionable within the borehole, the ring having an inner surface; and
a bone screw comprising a head and a shank, the head having a roughened, non-threaded outer surface that frictionally couples the head to the inner surface of the ring; and
wherein the ring allows the bone screw to be inserted into a bone at a desired angle relative to the plate, and wherein movement of the bone screw with respect to the ring is substantially inhibited during use.

40. The system of claim 39, wherein the ring is configured to substantially surround the head during use, and wherein rotating the bone screw rotates the ring when the ring and bone screw are frictionally coupled together.

41. The system of claim 39, wherein the outer surface of the head further comprises head threading, the head threading being complementary to ring threading on the inner surface of the ring.

42. The system of claim 41, wherein the ring threading has multiple starts to facilitate connection of the bone screw and the ring during use.

43. The system of claim 41, wherein the ring threading has a double start to facilitate connection of the bone screw and the ring during use.

44. The system of claim 41, wherein the ring threading has a triple start to facilitate connection of the bone screw and the ring during use.

45. The system of claim 41, wherein the shank comprises bone threading having a first pitch, and wherein the ring threading comprises a second pitch, the second pitch being substantially equal to the first pitch.

46. The system of claim 41, wherein the shank comprises bone threading having a first pitch, and wherein the ring threading comprises a second pitch, the second pitch being substantially equal to the first pitch, and wherein the pitch is predetermined to allow the plate to contact the bone when the bone screw is inserted within the bone and coupled to the ring.

47. The system of claim 39, wherein the ring is movable within the borehole such that the shank is rotatable in a substantially conical range of motion to allow the shank to be positioned at a selected angle relative to the plate.

48. The system of claim 39, wherein the ring comprises one or more slots to allow it to expand.

49. The system of claim 39, wherein the ring comprises one or more slots to allow it to contract.

50. The system of claim 39, wherein the borehole comprises an inner surface and a width across the borehole, the inner surface being curved such that the width varies in a direction axially along the borehole.

51. The system of claim 39, wherein the borehole comprises a substantially curvate inner surface, and wherein the ring further comprises a substantially curvate outer surface, the curvate outer surface being shaped to allow the ring to swivel within the borehole.

52. The system of claim 39, wherein the ring is configured to reside within the borehole without extending above an upper surface of the plate during use.

53. The system of claim 39, wherein the ring substantially surrounds the head of the bone screw, and wherein the bone screw is capable of being angulated relative to the plate during use such that the head remains below the upper surface of the plate.

54. The system of claim 39, wherein the plate comprises a second borehole, and the system further comprises:
a second bone screw comprising a second head and a second shank the second head having a roughened outer surface; and
a second ring for coupling the second bone screw to the plate, the second ring being positionable within the second borehole between the plate and the second bone screw during use.

55. The system of claim 54, wherein the first shank is positioned at a first oblique angle relative to the plate during use, and wherein the second shank is positioned at a second oblique angle relative to the plate during use, and wherein the first shank and the second shank extend in diverging directions relative to each other during use.

56. The system of claim 54, wherein the first shank is positioned at a first oblique angle relative to the plate during use, and wherein the second shank is positioned at a second oblique angle relative to the plate during use, and wherein the first shank and the second shank extend in converging directions relative to each other during use.

57. The system of claim 39, wherein the ring is rotatable within the borehole so that the shank is positionable through the ring at a selectable angle that is less than about 15 degrees relative to a plane substantially perpendicular to the plate.

58. The system of claim 39, wherein the ring comprises a plurality of slots extending from a bottom and a top of the ring to a middle portion of the ring.

59. The system of claim 39, wherein the inner surface of the ring is roughened to engage the roughening of the head.

60. The system of claim 39, wherein the ring is configured to substantially surround the head during use, and wherein rotating the bone screw rotates the ring when the ring and bone screw are frictionally coupled.

61. A spinal fixation system, comprising:
a plate for stabilizing a spine, the plate comprising a borehole, the borehole comprising a substantially curvate inner surface;
a bone screw for coupling the plate to a bone, the bone screw comprising a head, the head comprising threading and being positionable within the borehole during use; and
a ring for inhibiting backout of the bone screw from the plate, the ring being positionable within the borehole between the plate and the head during use, the ring comprising a substantially curvate outer surface and an inner surface having ring threading disposed thereon for engaging the threading on the head during use;
wherein the threading of the head couples the ring to the bone screw, and wherein the coupled head and ring are configured to allow advancement of a shank of the bone screw into the bone without fixedly coupling the ring to the plate during use.

62. The system of claim 61, wherein the ring is configured to substantially surround the head during use, and wherein rotating the bone screw rotates the ring when the ring and bone screw are coupled together.

63. The system of claim 61, wherein the ring threading has multiple starts to facilitate connection of the bone screw and the ring during use.

64. The system of claim 61, wherein the ring threading has a double start to facilitate connection of the bone screw and the ring during use.

65. The system of claim 61, wherein the ring threading has a triple start to facilitate connection of the bone screw and the ring during use.

66. The system of claim 61, wherein the ring is configured to reside within the borehole without extending above the upper surface of the plate during use.

67. The system of claim 61, wherein the plate comprises an upper surface and lower surface, and wherein the borehole extends between the upper and lower surfaces, the borehole comprising a width that varies in a direction axially along the borehole, and wherein the ring is disposed within the borehole, the ring further comprising an outer ring width that is greater than about the width of the borehole proximate the upper and lower surfaces, the outer ring width being sized relative to the width of the borehole proximate the upper and lower surfaces to substantially inhibit the ring from being removed from the borehole.

68. A spinal fixation system, comprising:
   a plate for stabilizing a spine, the plate comprising a borehole;
   a bone screw comprising a head and a shank for coupling the plate to a bone; and
   a ring comprising a non-threaded inner surface, the ring configured to couple the bone screw to the plate, wherein the ring is positionable within the borehole between the plate and the bone screw during use;
   wherein the inner surface of the ring is roughened to promote frictional engagement between the ring and the head, and wherein movement of the bone screw with respect to the ring is substantially inhibited during use.

69. The system of claim 68, wherein the ring is configured to substantially surround the head during use, and wherein rotating the bone screw rotates the ring when the ring and bone screw are frictionally engaged.

70. The system of claim 68, wherein the ring is movable within the borehole such that the shank is rotatable in a substantially conical range of motion to allow the shank to be positioned at a selected angle relative to the plate.

71. The system of claim 68, wherein the ring comprises one or more slots to allow it to expand.

72. The system of claim 68, wherein the ring comprises one or more slots to allow it to contract.

73. The system of claim 68, wherein the borehole comprises an inner surface and a width across the borehole, the inner surface being curved such that the width varies in a direction axially along the borehole.

74. The system of claim 68, wherein the borehole comprises a substantially curvate inner surface, and wherein the ring further comprises a substantially curvate outer surface, the curvate outer surface being shaped to allow the ring to swivel within the borehole.

75. The system of claim 68, wherein the plate comprises an upper surface and lower surface, and wherein the ring comprises an outer surface and an outer ring width, and wherein the borehole comprises a substantially curvate inner surface and a width defined across the inner surface, the width of the borehole varying in a direction axially along the borehole, and wherein the width of the borehole is greater than about the outer ring width at a location between the upper and lower surface, and wherein the width of the borehole is not greater than the outer ring width proximate the upper and lower surfaces.

76. The system of claim 68, wherein the plate comprises an upper surface and a lower surface, and wherein the borehole extends between the upper and lower surfaces, the borehole comprising a width that varies in a direction axially along the borehole, and wherein the ring is disposed within the borehole, the ring further comprising an outer ring width that is greater than about the width of the borehole proximate the upper and lower surfaces, the outer ring width being sized relative to the width of the borehole proximate the upper and lower surfaces to substantially inhibit the ring from being removed from the borehole.

77. The system of claim 68, wherein the ring is configured to reside within the borehole without extending above an upper surface of the plate during use.

78. The system of claim 68, wherein the ring substantially surrounds the head of the bone screw, and wherein the bone screw is capable of being angulated relative to the plate during use such that the head remains below the upper surface of the plate.

79. The system of claim 68, wherein the outer surface of the head is roughened.

80. A spinal fixation system, comprising:
   a plate for stabilizing a spine, the plate comprising a first pair of boreholes, a second pair of boreholes, and a midline borehole, the midline borehole positioned between the first and the second pairs of boreholes;
   a plurality of bone screws, each of the bone screws comprising a head and a shank for coupling a portion of the plate to bone, the heads of the bone screws comprising threading, and
   a plurality of rings for inhibiting backout of the bone screws from the plate, each of the rings being positionable within one of the boreholes between the plate and one of the bone screws during use, wherein each of the rings comprises ring threading for engaging head threading of the bone screws during use;
   wherein the rings allow the bone screws to be inserted into bone at desired angles relative to the plate;
   wherein the head threading of the bone screws couples the rings to the bone screws; and
   wherein the coupled heads and rings are configured to allow advancement of the shanks without the rings fixedly engaging the bone screws to the plate during use.

81. The system of 80, wherein each of the rings are configured to substantially surround the heads of the bone screws during use.

82. The system of 80, wherein the threading of each ring has multiple starts to facilitate connection of the bone screws and the rings during use.

83. The system of 80, wherein the threading of each ring has a double start to facilitate connection of the bone screws and the rings during use.

84. The system of 80, wherein the threading of each ring has a triple start to facilitate connection of the bone screws and the rings during use.

85. The system of 80, wherein each of the rings are configured to reside within the boreholes without extending above an upper surface of the plate during use.

86. The system of 80, wherein each of the boreholes comprises a substantially curvate inner surface, and wherein each of the rings further comprises a substantially curvate outer surface, the curvate outer surface being shaped to allow each of the rings to swivel within each of the boreholes.

87. The system of 80, wherein the plate comprises an upper surface and a lower surface, and wherein the boreholes extend between the upper and lower surfaces, and each borehole comprising a width that varies in a direction axially along the borehole, and wherein each of the rings is disposed within the boreholes, the rings further comprising an outer ring width that is greater than about the width of the boreholes proximate the upper and lower surfaces, the outer ring width being sized relative to the width of the borehole proximate the upper and lower surfaces to substantially inhibit each of the rings from being removed from each borehole.

88. A spinal fixation plate, comprising;
   a borehole extending between an upper surface and a lower surface of the plate, the borehole comprising a width that varies in a direction axially along the borehole; and
   a ring disposed within the borehole, the ring further comprising a roughened, non-threaded inner surface and an outer ring width that is greater than about the width of the borehole proximate the upper and lower surfaces, the outer ring width being sized relative to the width of the borehole proximate the upper and lower surfaces to substantially inhibit the ring from being removed from the borehole, wherein the roughened inner surface of the ring is configured to engage an outer surface of a head of a bone screw, and wherein the ring is configured to allow the bone screw to be angularly inserted into a bone relative to the plate.

89. The plate of claim 88, wherein the ring is configured to substantially surround the head during use, and wherein rotating the bone screw rotates the ring when the ring and bone screw are engaged.

90. The plate of claim 88, wherein the ring comprises a slot to allow it to contract.

91. The plate of claim 88, wherein the ring comprises a plurality of partial slots extending from top and bottom surfaces of the ring.

92. The system of claim 88, wherein the borehole comprises a substantially curvate inner surface, and wherein the ring further comprises a substantially curvate outer surface, the curvate outer surface being shaped to allow the ring to swivel within the borehole.

93. The plate of claim 88, wherein the ring is configured to reside within the borehole without extending above an upper surface of the plate during use.

94. The plate of claim 88, further comprising ring threading on the inner surface of the ring, wherein the ring threading has multiple starts to facilitate connection of the bone screw and the ring during use.

95. The plate of claim 88, further comprising ring threading on the inner surface of the ring, wherein the ring threading has a double start to facilitate connection of the bone screw and the ring during use.

96. The plate of claim 88, further comprising ring threading on the inner surface of the ring, wherein the ring threading has a triple start to facilitate connection of the bone screw and the ring during use.

97. The plate of claim 88, wherein the ring is configured to reside within the borehole without extending above an upper surface of the plate during use.

98. The plate of claim 88, wherein the plate further comprises:
   additional boreholes extending between the upper and lower surface of the plate, each additional borehole comprising a variable width; and
   additional rings disposed within each of the additional boreholes, each additional ring comprising a roughened inner surface and an outer ring width that is greater than about the width of the additional boreholes proximate the upper and lower surfaces, the additional rings outer ring width being sized relative to the width of the additional boreholes proximate the upper and lower surfaces to substantially inhibit the additional rings from being removed from the additional boreholes, and wherein the roughened inner surface of each additional ring is configured to engage an outer surface of a head of a bone screw, and wherein the rings are configured to allow the bone screws to be angularly inserted into bone relative to the plate.

* * * * *

UNITED STATES PATENT AND TRADEMARK OFFICE
CERTIFICATE OF CORRECTION

PATENT NO. : 6,454,769 B2
DATED : September 24, 2002
INVENTOR(S) : Wagner et al.

It is certified that error appears in the above-identified patent and that said Letters Patent is hereby corrected as shown below:

Column 14,
Line 41, please delete claim 31.

Signed and Sealed this

Tenth Day of June, 2003

JAMES E. ROGAN
*Director of the United States Patent and Trademark Office*

Disclaimer

6,454,769 B2 — Erik J. Wagner, Austin, TX (US); Robert Jones, Austin, TX (US). SYSTEM AND METHOD FOR STABILIZING THE HUMAN SPINE WITH A BONE PLATE. Patent dated September 24, 2002. Disclaimer filed October 7, 2002, by the assignee, Spinal Concepts, Inc.

Hereby enters this disclaimer to claim 31, of said patent.

*(Official Gazette October 14, 2008)*